United States Patent
Matic et al.

(10) Patent No.: US 11,045,126 B2
(45) Date of Patent: Jun. 29, 2021

(54) SYSTEM AND A METHOD FOR ENABLING RESPONSIVE COGNITIVE BEHAVIORAL THERAPY

(71) Applicant: TELEFONICA INNOVACION ALPHA S.L., Madrid (ES)

(72) Inventors: Aleksandar Matic, Madrid (ES); Oliver Thomas Harisson, Madrid (ES); Remko Vermeulen, Madrid (ES)

(73) Assignee: KOA HEALTH B.V., Amsterdam (NL)

( * ) Notice: Subject to any disclaimer, the term of this patent is extended or adjusted under 35 U.S.C. 154(b) by 20 days.

(21) Appl. No.: 16/345,482

(22) PCT Filed: Oct. 24, 2017

(86) PCT No.: PCT/EP2017/077106
§ 371 (c)(1),
(2) Date: Apr. 26, 2019

(87) PCT Pub. No.: WO2018/077844
PCT Pub. Date: May 3, 2018

(65) Prior Publication Data
US 2019/0246968 A1 Aug. 15, 2019

(30) Foreign Application Priority Data

Oct. 28, 2016 (EP) .................................. 16382494

(51) Int. Cl.
*A61B 5/16* (2006.01)
*A61B 5/00* (2006.01)
*G16H 20/70* (2018.01)
*G16H 50/30* (2018.01)
*G16H 40/67* (2018.01)

(52) U.S. Cl.
CPC .............. *A61B 5/16* (2013.01); *A61B 5/0022* (2013.01); *A61B 5/4848* (2013.01); *A61B 5/4866* (2013.01); *A61B 5/6802* (2013.01); *A61B 5/7264* (2013.01); *A61B 5/7275* (2013.01); *G16H 20/70* (2018.01); *G16H 40/67* (2018.01); *G16H 50/30* (2018.01)

(58) Field of Classification Search
None
See application file for complete search history.

(56) References Cited

U.S. PATENT DOCUMENTS

2011/0119212 A1\* 5/2011 De Bruin .................. A61B 5/00
706/12
2012/0290266 A1 11/2012 Jain et al.
2015/0179079 A1 6/2015 Rodriguez, Jr. et al.

FOREIGN PATENT DOCUMENTS

WO 2009/144502 A1 12/2009

OTHER PUBLICATIONS

Mark Matthews et al., "Tracking Mental Well-Being: Balancing Rich Sensing and Patient Needs," Computer, IEEE Computer Society, Apr. 1, 2014, pp. 36-43, vol. 47, No. 4.
(Continued)

*Primary Examiner* — Brian T Gedeon
(74) *Attorney, Agent, or Firm* — Sughrue Mion, PLLC

(57) ABSTRACT

Method and System for Enabling Responsive Cognitive Behavioral Therapy by automatic monitoring of patients' behavior, determining significant changes of behavior and the progress of therapy and engaging with patients and/or therapists.

16 Claims, 2 Drawing Sheets

(56) References Cited

OTHER PUBLICATIONS

Written Opinion of the International Searching Authority of PCT/EP2017/077106 dated Jan. 18, 2018.
International Search Report of PCT/EP2017/077106 dated Jan. 18, 2018.

* cited by examiner

SYSTEM AND A METHOD FOR ENABLING RESPONSIVE COGNITIVE BEHAVIORAL THERAPY

CROSS REFERENCE TO RELATED APPLICATIONS

This application is a National Stage of International Application No. PCT/EP2017/077106 filed Oct. 24, 2017, claiming priority based on European Patent Application No. 16382494.9 filed Oct. 28, 2016.

TECHNICAL FIELD

The present invention is directed, in general, to the field of medical systems and methods monitoring. In particular, the invention relates to a system and to a method for enabling responsive Cognitive Behavioral Therapy (CBT) by automatic monitoring of patient's behavior parameters that are relevant for adapting the frequency and/or the content and/or the structure and/or the interaction design of CBT sessions that a patient is attending, determining significant changes of behavior, assessing the progress of therapy and engaging with patients and/or therapists.

BACKGROUND OF THE INVENTION

CBT has become a standard in treating a diverse set of (mostly mental) problems. The studies have demonstrated that CBT is effective in treating depression and anxiety disorders, obsessive compulsive disorder (OCT), bipolar disorder, eating disorder, borderline personality disorder, post-traumatic stress disorder, substance abuse and many others. Moreover, past years have witnessed an emerging development of digital implementations of CBT (such as web-, mobile phone-, tablet- or personal computer-based CBT applications), with a varying success with respect to different problems and disorders.

Success of CBT heavily depends on a continuous monitoring of patients' progress and co-occurring changes in behavior, thoughts and emotions. In the current practice, the assessment of the said changes is performed in an episodic way, typically during CBT sessions with therapist. However, in such way therapists gain only a snapshot of the current patient state; moreover, describing past behaviors is based on patients' self-reports (or diaries) that suffer from memory dependence, subjectivity and recall bias. This puts additional challenges for therapists who need to spot positive or negative (often subtle) changes in behavior related to the CBT progress. On the other hand, technology based CBT implementations are designed in one-size-fits-all fashion, and only rarely such applications adapt the CBT programs by using rather simple "if-this-than-that" algorithms based on the inputs from self-reports.

Some known patent applications in the field include:

US patent application US-A1-20080214903 disclosing a system and method for monitoring one or more physiological parameters of a user. The method of this invention includes obtaining values of the physiological parameters of the user from one or more wearable sensor modules. Signals indicative of values of the one or more physiological parameters are wirelessly transmitted to a mobile monitor. The signals are processed in real time using expert knowledge, and one or more indications of results of the processing are provided to the mobile unit.

U.S. Pat. No. 8,979,730 disclosing a system and a method providing an automatic assessment of the presence/severity of the sleep problem and its exact nature. The assessment is based on qualitative information about sleep patterns, insomnia-related factors and daytime consequences, as well as quantitative information about sleep patterns measured by a sensor. By combining the different sources of information (subjective as well as objective data), the diagnosis gives more insight into the nature of the sleep problem and is therefore more accurate.

US patent application US-A1-20100280562 disclosing methods for identifying and measuring pharmacodynamic biomarkers of neuropsychiatric disease, and for monitoring a subject's response to treatment. For example, materials and methods for monitoring the effectiveness of vague nerve stimulation in a subject having a neuropsychiatric disease.

SUMMARY OF THE INVENTION

Present invention provides a method and a system for monitoring one or multiple groups of behavioral parameters of a user/patient that are relevant for adapting the frequency and/or the content and/or the structure and/or the interaction design of Cognitive Behavioral Therapy (CBT) sessions that the user/patient is attending.

The system relies on data collected from one or more sensors, from historical log-records and/or from ongoing usage of personal devices to extract behavioral parameters that are relevant for the problem that the CBT addresses and that can be indicative of the CBT progress. Assessing the progress of CBT and prompting changes in CBT sessions, related to their frequency and/or content may be performed in two ways:

1) by analyzing the behavioral vectors using expert knowledge i.e. the system may inform a therapist about important behavioral changes thus augmenting the traditional form of CBT sessions as it enables therapist to respond promptly, and/or
2) by applying statistical approaches and machine learning algorithms on prior knowledge containing assessed progress of CBT progression with co-occurring behavioral vectors, and querying such models using behavioral parameters collected about a new user/patient.

Embodiments of the proposed invention are described according to appended claims 1 to 10, and in subsequent sections related to the detailed description of the invention and of the preferred embodiments.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF THE INVENTION AND OF PREFERRED EMBODIMENTS

Figure 1:
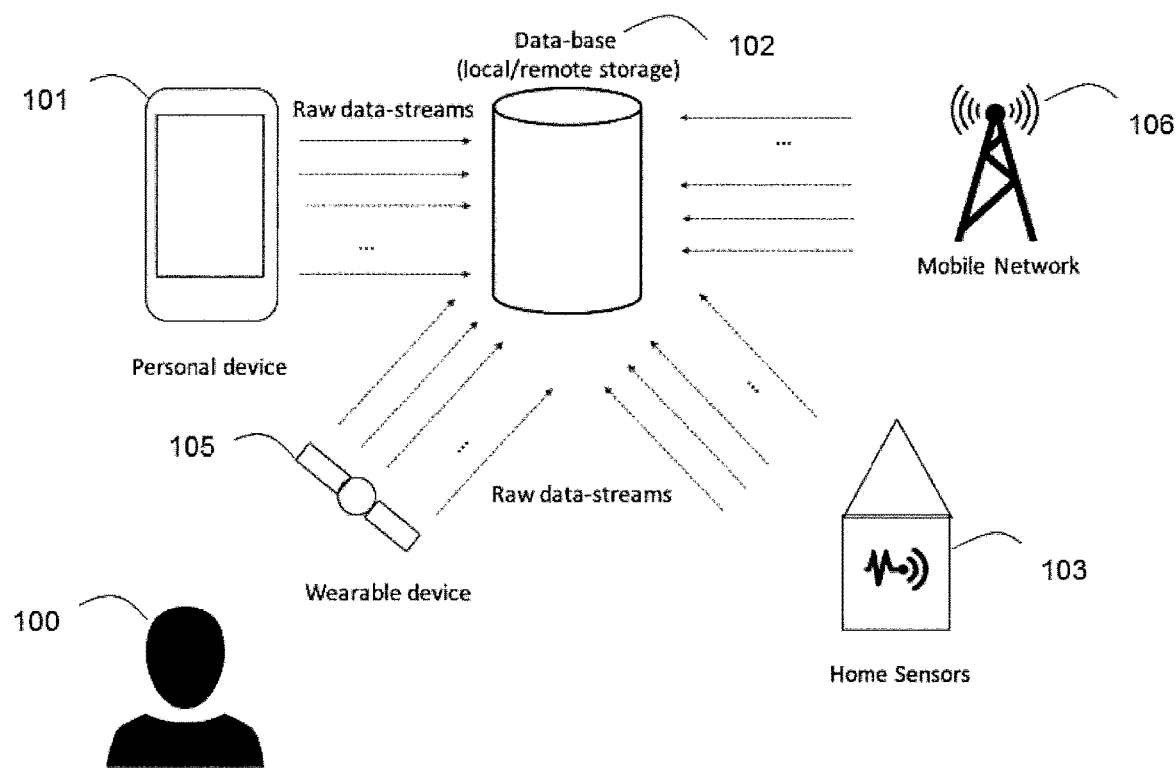
FIG. 1 schematically shows some of the elements of the invention to collect and store data from a user/patient.
Figure 2:
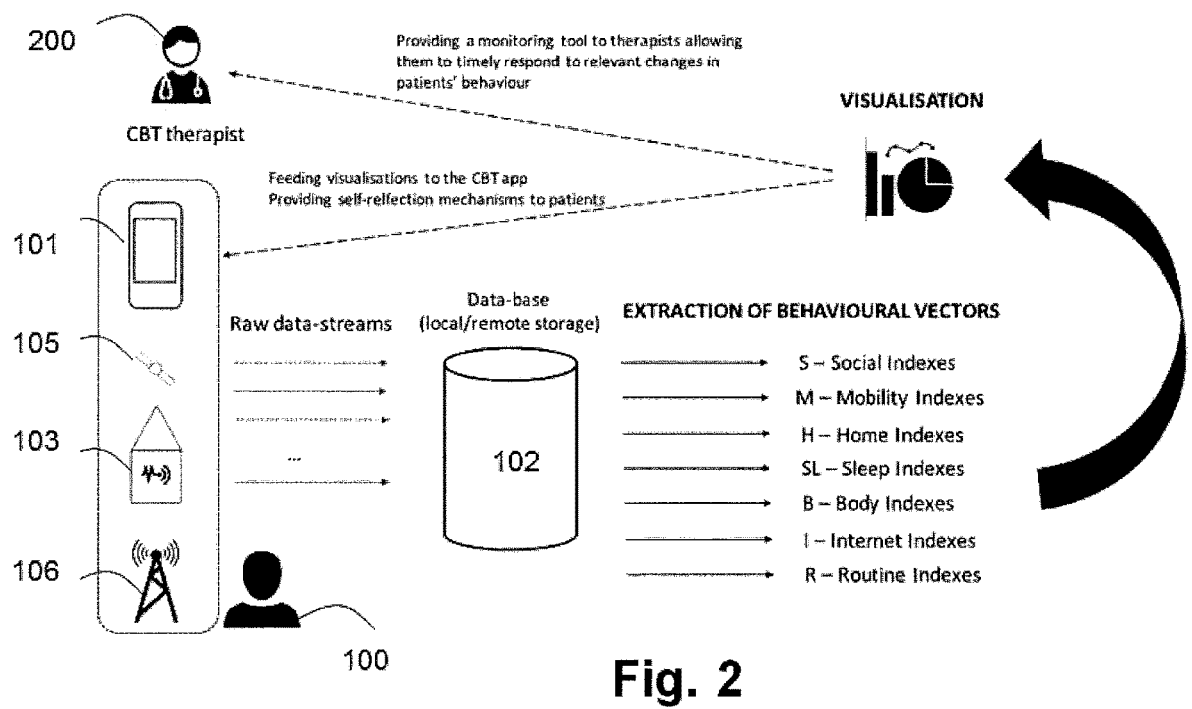
FIG. 2 schematically shows the general architecture of the invention to collect and store data from a user/patient, to extract the behavioral vectors and to produce a report delivered to a therapist, according to an embodiment of the present invention.
Figure 3:
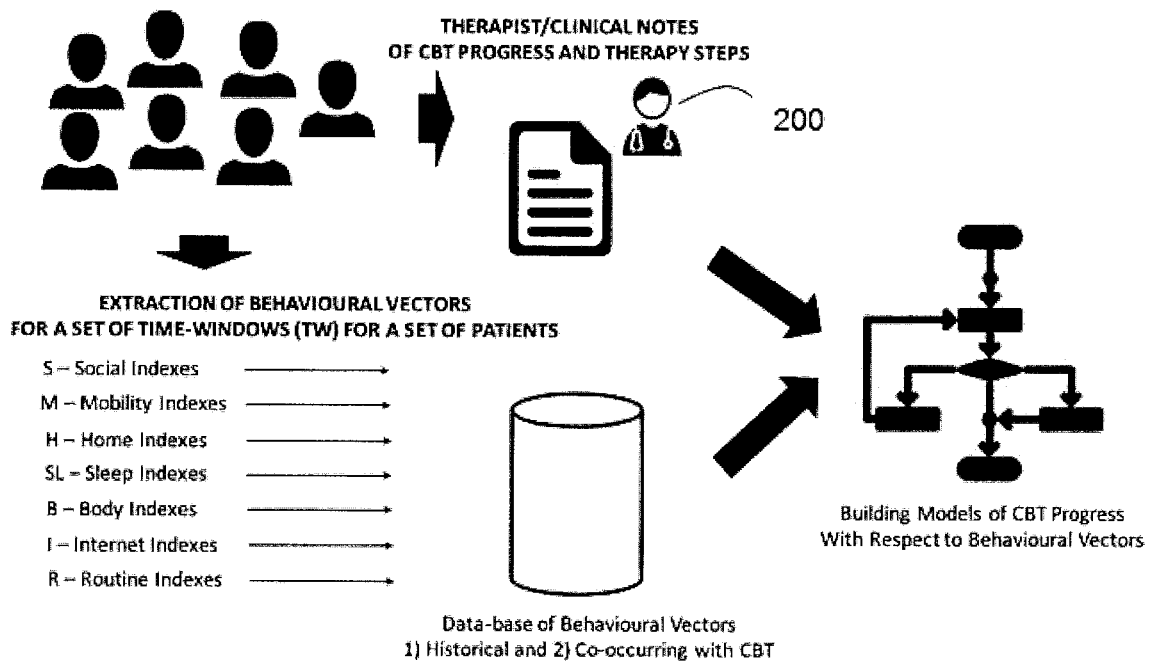
FIG. 3 schematically shows the general architecture of the invention to collect and store data from a group of users/patients to build models of CBT progress with respect to behavioral vectors, according to an embodiment of the present invention.
Figure 4:
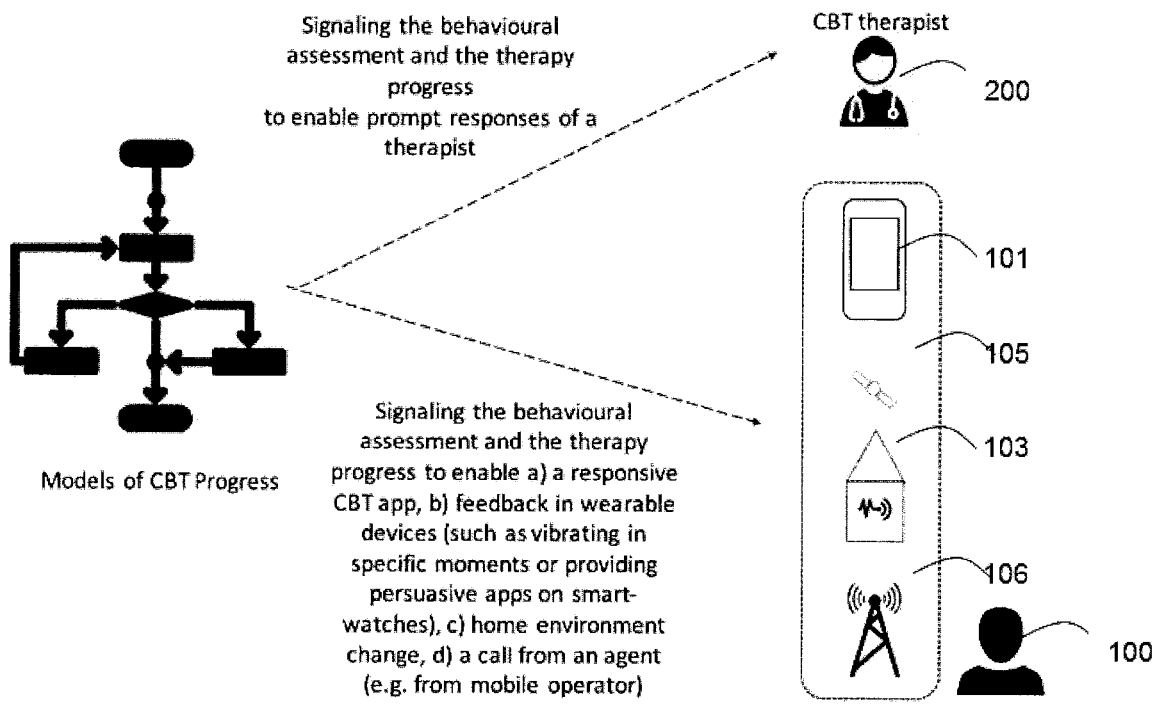
FIG. 4 schematically shows the general architecture of the invention for signaling the behavioral assessment and the therapy progress to a CBT therapist and/or to the user/patient according to an embodiment of the present invention.

Present invention addresses one of the main challenges in psychiatry practice of constant monitoring of users/patients 100 and recognizing important changes as soon as they happen to react promptly (and sometimes to prevent negative outcomes) by adapting the ongoing CBT or prompting new CBT sessions. When it comes to monitoring of behavior, an important aspect is to be as unobtrusive as possible because any interference caused by monitoring can result in provoking non-natural behaviors.

To that end, present invention relies on data collected from technologies that users/patients 100 are already using (such as personal devices 101 for example a mobile phone, wearable devices 105 such as fitness trackers, home sensors 103, etc.) i.e. that are not additionally imposed to them. Present invention can rely on the usage of mobile network data, which results in a fully passive way of behavioral monitoring as it does not require any locally installed application and it is invisible from the user's perspective. This can work with any mobile phone model, given that the user 100 already has this device that is nowadays habitually carried by users. The invention can be extended to include any other home sensor or wearable that a CBT user already has, or in case of possessing a smart-phone the data can be collected by an APP.

Present invention uses the software that collects all the data, produces relevant behavioral indexes and by applying machine learning techniques automatically assesses the progress of the ongoing CBT. Moreover, present invention can produce a report which can be delivered to a therapist 200, to the user 100 or to a technology-based CBT application in order to adapt the program. Therefore, present invention supports both therapists or technology-based CBT implementations.

Table 1 lists changes in behavior that can be detected in an automatic way using data gathered from one or more of the said technologies and that may be linked to a number of psychiatric conditions (Table 1 provides a limited list of examples).

TABLE 1

Groups of behavioral indexes relevant for example disorders treated with CBT (specific behavioral indexes are elaborated in preferred embodiments)

| | Social Indexes | Mobility Indexes | Home indexes | Sleep indexes | Body-sensor indexes | Internet usage indexes | Routine indexes |
|---|---|---|---|---|---|---|---|
| Depression-related disorders | X | X | X | X | X | X | X |
| Anxiety-related disorders | X | X | X | X | X | X | X |
| Obsessive compulsive disorder (OCT) | X | X | X | | | | X |
| Bipolar disorder | X | X | X | X | X | X | X |
| Eating disorders | X | X | X | X | X | | X |
| Borderline personality disorder | X | X | X | X | X | | X |
| Post-traumatic stress disorder | X | X | X | X | X | | X |
| Substance abuse | X | X | X | X | X | | X |

Behavioral Indexes:

Behavioral indexes represent descriptors (such as descriptive statistics, topical descriptors, tags based on a specifically defined dictionary) of a) dynamics of one or multiple data-sources, b) content-related information from data-sources. These behavioral indexes can be extracted and accumulated in different time-windows (TW) including per hour, per multiple-hours (such as windows defined as morning, afternoon, evening, night), per day, per week, per month, or per year.

Vector of Social Indexes:

Vector of social indexes $S=(s1, s2 \ldots sn)$ is a set of descriptors related to electronically mediated (such as calls, SMS, internet-based messengers, etc.) or in-person social interactions where $s1, s2 \ldots sn$ correspond to descriptors of social activities computed in a TW. The examples of $s1, \ldots, sn$ include (but are not limited to) a number of incoming/outgoing calls, entropies of calls and contacts, distribution characteristics of inter-call or inter-message durations, number of unique correspondents, number of strong/medium/weak ties of contacts in a social network (defined specifically for an intended use-case), duration of social activities (e.g. time spent in in-person social interactions, in calls, using messengers, etc.), time spent using online social networks, etc.

Vector of Mobility Indexes:

Vector of mobility indexes $M=(m1 \ldots mn)$ is a set of descriptors related to user's whereabouts where $m1, m2, \ldots$ . mn correspond to descriptors of mobility patterns computed in a time-window TW. The examples of m1, . . . , mn include (but are not limited to) a number of visited places, entropy of duration spent at unique visited places, newly visited places, radius of gyration, max distance from home, max distance from work, etc.

Vector of Home Indexes:

Vector of home indexes H=(h1, h2, . . . hn) is a set of descriptors related to behavior at home where h1, . . . hn correspond to descriptors of home stay patterns computed in a time-window TW. The examples of h1, . . . , hn include (but are not limited to) a duration of staying at home, duration of staying in each room, time arriving to or leaving home, etc.

Vector of Sleep Indexes:

Vector of sleep indexes SL=(sl1, sl2 . . . sln) is a set of descriptors related to sleep where sl1, sl2 . . . sln correspond to descriptors of sleep patterns computed in a time-window TW. The examples of sl1, sl2 . . . sln include (but are not limited to) a duration of sleep, time to go to sleep, time of waking up, label for interrupted sleep, etc.

Vector of Body-Sensor Indexes:

Vector of body-sensor indexes B=(b1, b2 . . . bn) is a set of descriptors captured using wearable sensors where b1, b2 . . . bn correspond to physical or physiological patterns computed in a time-window TW. The examples of b1, b2 . . . bn include (but are not limited to) a duration of quantified physical movements (such as steps, calories, metabolic-equivalent measures, etc.), sedentary time, heart-rate, heart-rate variability, galvanic-skin response, etc.

Vector of Internet-Usage Indexes:

Vector of internet-usage indexes I=(i1, i2 . . . in) corresponds to descriptors of internet usage patterns computed in a time-window TW. The examples of i1 . . . in related to dynamics of using internet include (but are not limited to) duration of using internet, amount of downlink or uplink data-volumes, duration of using mobile versus Wi-Fi internet, etc. The examples of i1 . . . in related to the content of using internet include, but not limited to, entropy of different categories of websites (where categories can correspond to specifically defined dictionaries such as custom-made or public ones such as "alexa"), presence of certain categories, vectors of topical interests, etc.

Routine Indexes:

Routine indexes R=(RS, RM, RH, RSL, RB, RI) represent a vector constituted of vectors of parameters that describe distributions of vectors S, M, H, SL, B, I within multiple time-windows TW. For example, 7 consecutively extracted vectors S, M, H, SL, B, I, each computed per day time-window TW, can be used to produce R vector which corresponds to distribution of all behavioral indexes over one week. Vectors RS=(rs1, rs2, . . . rsn), RM=(rm1, rm2, . . . rmn), RH=(rh1, rh2, . . . , rhn), RSL=(rsl1, rsl2, . . . rsln), RB=(rb1, rb2, . . . , rbn), RI=(ri1, ri2, . . . rin) can be consisted of various distribution characterization mechanisms. For example, rs1, rm1, rh1, rsl1, rb1, ri1 can be values that represent the measure of a central tendency (mean, median, etc.) for each of behavioral index vectors; rs2, rm2, rh2, rsl2, rb2, ri2 can be a measure of dispersion (such as variance, standard deviation, etc.); rs3, rm3, rh3, rsl3, rb3, ri3 can be a measure of fitness to a specific distribution (such as Kolmogorov-Smirnoff test parameters, or p-value of distribution fit, etc.) or a measure of skewness, kurtosis, or similar.

In an embodiment, only mobile network data is used to passively collect the logs of mobile phone usage and of locations of users. In this embodiment, behavioral indexes S, M, H, and I can be directly calculated using Call Detailed Records (CDRs) that contain all the logs of calls and messages, Internet logs, and network events (that typically contain periodic samples of an approximate geographical location). Whereas B vector cannot be computed, SL vector of sleep patterns can be indirectly captured by using mobile network data as an indicative proxy to sleep by applying the following set of rules related to sleep inference: last activity detected after a specific hour (e.g. 9 pm) without a new detected activity within next N number of hours (e.g. N=3 hours) corresponds to the time to go to bed. The first detected activity after a specific hour (e.g. 5 am) corresponds to the time of waking up. In case of detecting any activity between the two (going to bed and waking up time-stamps) the event is labelled as interrupted sleep. The activity event corresponds to any phone activity logged in mobile network data (such as internet usage, call, message, and change of location).

In another embodiment, mobile network data can be complemented with home or body sensors that enrich the behavioral vectors B and H.

In another embodiment, given the availability of a smartphones, a mobile APP can be used to complement or to be used independently for extraction of S, M, H, SL, B, I behavioral vectors.

In another embodiment, behavioral vectors can be complemented with patients' self-report data.

In each of these embodiments, extraction of Routine indexes corresponds to the same process described above.

Present invention provides a number of CBT embodiments. A non-exhaustive list thereof is presented as methods, systems, apparatus and/or a devices or computer programs having the features as follows:

According to a first embodiment, or automated collection of behavioral data, present invention includes:

a) User mobile network data (including both retrospective and ongoing samples, where possible)

b) Data collected from user smartphone c) Data collected from other data sources (connected via the user smartphone or directly sending the data to the server).

According to a second embodiment, or analysis of data set-out in the first embodiment to extract and visualize relevant behavioral indexes over short and long term (to users, therapists, informal caregivers, etc.), present invention comprises considering, for instance:

a) Sleep duration and sleep disturbances b) Physical activity (calories, distance travelled, steps, etc.)

c) Social activity (phone plus F2F; the latter can be simplified as a detection of surrounding voice)

d) Time spent at home e) Contextual information (e.g. visiting places with a lot of people, going to nature, etc.)

f) Indexes that represent circadian rhythms/daily routines

According to a third embodiment, present invention describes symptom detection by means of performing a sub-embodiment, on how to develop novel digital health biomarkers for conditions:

a) Running machine learning algorithms using an extensive set of complex behavioral indexes to detect significant changes in behavior patients, and/or b) Quantitative and qualitative comparison of behavior among patient sample and between patient and healthy users, and/or c) Identify biomarkers of both positive and negative behavioral changes with respect to the patient progress Additionally, another sub-embodiment is performed, developing novel ways to report symptoms including: a)

technology supported ways of indicating symptoms (Many patients are embarrassed and ashamed of their symptoms and they are reluctant to reveal them to family members, friends, or therapists (Conroy et al, 2008); and/or b) the examples include visual aids, voice recording, specifically designed chat-bots, and/or automatic analysis of selfie-photos, etc.

According to a fourth embodiment, present invention describes automatic Trait Analysis including:
a) Automatic clustering of patients based on different criteria (e.g. treatment parameters), and/or
b) Inference of traits and personal characteristics according to the established models (such as BIG-5), used as an input for adjusting the CBT program.

In this way, automatic labeling of user's characteristics can be applied for personalizing the content, structure, dynamics or interaction design of CBT programs.

According to a fifth embodiment, present invention describes changing the users' perception by means of:
Manipulating the utility function to their perception of themselves, people from their surroundings, and situations, and/or
Exploration of ability to shift user perception of benefits and costs of service use (as relates to subjective user utility function, Weber-Fechner Law, etc.), and/or
Exploration of ability to shift user perception of time (as relates to subjective user utility function, Weber-Fechner Law, etc.).

According to a sixth embodiment, present invention describes inference of predisposition to a specific condition including predisposition to a specific condition e.g. anxiety, depression detected through automatically collected behavioral data.

According to a seventh embodiment, present invention describes improving sustainability and compliance to the CBT therapy by:
a) applying to parameters relating to happiness status or condition preserving mechanisms, and/or
b) providing digital immediate rewards; and/or
b) User design to substantially increase rates of uptake, acceptability, and/or sustained user engagement particularly among population segments that show low rates of service use compared to demand (e.g., demographic, socio-economic groups).

According to an eighth embodiment, present invention describes maximizing effectiveness of the CBT therapy (delivered by therapist and/or by a mobile APP) by using the proposed system and method for:
a) selecting the matched CBT component(s) (and/or the matched behavioral change tool) to a specific person; and/or
b) selecting the appropriate moments for prompting patients to undergo the CBT session; and/or
c) selecting the appropriate channel to deliver one or more CBT sessions; and/or
d) allocating the appropriate amount of CBT sessions, their duration and frequency over time to a specific person, and/or
e) selecting the appropriate content of the CBT sessions, tailored to a specific user.

According to a ninth embodiment, present invention describes developing "plug-and-play" health data platform for integration of digital health services and hospital electronic health record (cf., Red Hat and Linux).

According to a tenth embodiment, present invention describes including social components for a) assessment; and/or b) treatment.

According to an eleventh embodiment, present invention describes how to link the automatically observed behavioral indexes to neuroscience, e.g., elements of the NIMH Research Domain Criteria (RDoC), functional imaging, neuroanatomic structures.

The various features of the invention described herein can be implemented in different methods/systems without departing from the invention. It should be noted that the foregoing embodiments are merely examples and are not to be construed as limiting the invention. The description of the embodiments is intended to be illustrative, and not to limit the scope of the claims. As such, the present teachings can be readily applied to other types of methods/systems and many alternatives, modifications, and variations will be apparent to those skilled in the art.

The invention claimed is:

1. A method for tracking behavior of a user undergoing Cognitive Behavioral Therapy (CBT), the method comprising:
a) collecting data from historical log-records of a mobile phone of a user undergoing CBT for a defined period of time, the collecting being prior to attendance of a CBT session by the user;
b) producing a plurality of behavioral indices of the user by implementing an algorithm using the data collected from the historical log-records, the plurality of behavioral indices comprising a social index indicating a social interaction of the user, a mobility index indicating a pattern of mobility of the user, and an Internet-usage index indicating a pattern of internet usage of the user;
c) assessing, by the algorithm, a progress of CBT of the user by at least applying machine learning techniques to the produced plurality of behavioral indices;
d) producing, by the algorithm, a report indicative of the progress of the user in the CBT session based on a result of the assessing; and
e) selecting at least one of a channel, a content, and an amount of the CBT session for the user based on the plurality of behavioral indices.

2. The method of claim 1, further comprising delivering the produced report to the user, to a therapist and/or to a computer program that provides the CBT to the user.

3. The method of claim 1, wherein the collected data is further stored in a database, or storage device, prior to the attendance of the CBT session by the user.

4. The method of claim 1, further comprising establishing a base-line behavior of the user using the plurality of behavioral indices.

5. The method of claim 1, wherein the algorithm further comprises producing a plurality of vectors indices using the collected data, and the method further comprising using the plurality of behavioral indices and the plurality of vector indices to characterize behavior of the user during the period of undergoing the CBT and/or after the CBT.

6. The method of claim 5, wherein the period ranges from one to a few dozens of weeks during and after the CBT.

7. The method of claim 2, further comprising selecting a group of users from a historic database, and performing steps a) to d) for the selected group of users, wherein respective reports produced for the selected group of users are used as ground-truth for the therapist and/or for the computer program.

8. A system for tracking behavior of a user undergoing Cognitive Behavioral Therapy (CBT), the system comprising:

one or more sensors including a personal computing device, a wearable device and/or a home sensor adapted and configured to collect data of user undergoing CBT for a defined period of time and to transfer the collected data to at least one server;

the at least one server including one or more processors, wherein the collecting in step a) of claim 1 comprises collecting data from the one or more sensors, and wherein the one or more processors being adapted and configured to implement an algorithm to perform steps b) to d) of claim 1.

9. The system of claim 8, further comprising a database, local or remote, adapted and configured to store the collected data.

10. The system of claim 8, wherein the collected data is stored locally on the one or more sensors or remotely on the server.

11. The method of claim 1, wherein the collecting comprises collecting data from one or more sensors and/or from ongoing usage of personal devices of the user.

12. The method of claim 1, wherein the social index, the mobility index, and the Internet-usage index are obtained based on Call Detailed Records (CDRs) of the mobile phone, the CDRs including logs of calls and messages, Internet logs, and network events.

13. The method of claim of claim 12, wherein the plurality of behavioral indices further comprise a sleep index indicting a sleep pattern of the user, and wherein the sleep index is determined based on the CDRs of the mobile phone.

14. The method of claim 1, further comprising:

e) executing an machine learning algorithm by using the plurality of behavioral indices to detect a change in behavior of the user;

f) performing comparison of behavior among patient samples and between the user and samples of healthy users; and g) identifying, based on a result of the comparison, respective biomarkers of a positive behavioral change and a negative behavioral change with respect to the progress of the CBT.

15. The method of claim 1, wherein different combinations of the plurality of behavioral indices are used to assess the progress of the CBT that address different psychiatric conditions.

16. The method of claim 1, wherein the plurality of behavioral indices further comprise a home index indicating a pattern of the user's behavior at home detected by one or more home sensors.

* * * * *